United States Patent
Grasruck et al.

(10) Patent No.: US 8,295,915 B2
(45) Date of Patent: Oct. 23, 2012

(54) METHOD AND COMPUTATIONAL UNIT FOR MEASURING THE FLOW RATE OF A CONTRAST AGENT IN A VESSEL OF A PATIENT

(75) Inventors: Michael Grasruck, Erlangen (DE); Bernhard Schmidt, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 921 days.

(21) Appl. No.: 12/232,520

(22) Filed: Sep. 18, 2008

(65) Prior Publication Data

US 2009/0086882 A1   Apr. 2, 2009

(30) Foreign Application Priority Data

Sep. 27, 2007   (DE) .......................... 10 2007 046 281

(51) Int. Cl.
 *A61B 6/00*   (2006.01)
(52) U.S. Cl. ............... 600/431; 600/425; 378/4; 378/21
(58) Field of Classification Search .................. 600/407, 600/425, 427, 431; 378/87, 4, 21
See application file for complete search history.

(56) References Cited

U.S. PATENT DOCUMENTS

| 5,953,444 | A  | * | 9/1999 | Joseph et al. | 382/131 |
| 6,442,235 | B2 |   | 8/2002 | Koppe et al. | |
| 2006/0023840 | A1 | * | 2/2006 | Boese | 378/98.12 |
| 2007/0255135 | A1 | * | 11/2007 | Kalafut et al. | 600/431 |

FOREIGN PATENT DOCUMENTS

DE       10000185 A1    7/2001

* cited by examiner

*Primary Examiner* — Brian Casler
*Assistant Examiner* — Amanda Lauritzen
(74) *Attorney, Agent, or Firm* — Harness, Dickey & Pierce, P.L.C.

(57) ABSTRACT

A method and a computational unit are disclosed for measuring the flow rate of a contrast agent in a vessel of a patient by way of a computed tomography examination. The patient is scanned by x-rays emitted in a fan-shape from two planes and the absorption from a multiplicity of rotational angles is determined while the contrast agent propagates through the at least one vessel. According to at least one embodiment of the invention, a three-dimensional data record of local absorption data with the vessel which can be filled by a contrast agent is reconstructed; a set of x-rays which pass through this vessel is determined for a multiplicity of temporally subsequent rotational angles of the x-rays. By determining the changing absorption values along this vessel from the temporally subsequent vessel/ray-sets, the propagation velocity of the contrast agent in this vessel can be determined from the spatial and temporal change in the absorption values in this vessel.

16 Claims, 4 Drawing Sheets

METHOD AND COMPUTATIONAL UNIT FOR MEASURING THE FLOW RATE OF A CONTRAST AGENT IN A VESSEL OF A PATIENT

PRIORITY STATEMENT

The present application hereby claims priority under 35 U.S.C. §119 on German patent application number DE 10 2007 046 281.8 filed Sep. 27, 2007, the entire contents of which is hereby incorporated herein by reference.

FIELD

Embodiments of the invention generally relate to a method and/or a computational unit for measuring the flow rate of a contrast agent in at least one vessel of a patient by way of a computed tomography examination. In at least one embodiment it relates to a method and/or a computational unit in which the patient is scanned by x-rays emitted in a fan-shape on two planes and the absorption is determined from a multiplicity of rotational angles while the contrast agent propagates through the at least one vessel.

BACKGROUND

It is widely known that the flow rate in vessels can be determined by administering a contrast agent and simultaneously scanning the patient and generating computed tomography images for determining the flow rate of the contrast agent in a vessel of the patient. In this process, the patient is scanned a number of times by a rotating the x-ray source through at least 180°, with computed tomography image data being reconstructed from every 180° scan, in which the progress of a contrast agent perfusion in the vessels of the patient can be recognized. The flow rate can be determined based on this recognizable contrast agent propagation in the vessels of the patient.

In this case, it is a substantial problem that the scanning rate of CT systems, in particular of C-arm systems, is relatively slow, with the contrast agent during the scan or during a half rotation of the scan being able to propagate relatively quickly within a vessel, so that the reconstructed CT images do not represent snapshots in which a sharp edge of the propagation of a contrast agent bolus can be recognized.

SUMMARY

In at least one embodiment of the invention, a method is disclosed by which the rate of the contrast agent propagation in a vessel can be measured with a high temporal resolution by means of a CT examination.

The inventors have recognized that, in at least one embodiment, in a CT system, although the volume images reconstructed from half rotations of the system have insufficient temporal resolution, a combination of observing the obtained CT image data of a computed tomography examination and individual readings during the rotation of the recording system suffices to obtain high-resolution temporal information with respect to the spatial propagation of a contrast agent within a defined region of a patient, in particular within a vessel.

With respect to observing a vessel, it is necessary in this case to firstly determine the position of an observed vessel by means of a complete CT scan of a patient, with this preferably being done as soon as the vessel is completely filled with a contrast agent, so that the position of the vessel to be observed can be determined unambiguously. Once the profile of the vessel has been determined, it is possible to use the projections recorded previously as the vessel was successively being filled by contrast agent to determine those rays of each projection which pass through the observed vessel. If this is done for a multiplicity of projections arranged successively in time, it is possible to determine the contrast agent front within a vessel by locating the increasing absorption which occurs there with a temporal resolution which corresponds to the interval between the individual readings. So that the absorption data is influenced as little as possible by the remaining absorption of the patient when the rays pass through, the remaining absorption of the patient can be removed by calculation from the absorption data of those rays which intersect the vessel on the basis of a scan rotation without a contrast agent and the absorption data or projections recorded in the process, or on the basis of a reconstructed tomographic image data record, so that the change of absorption within the vessel is only determined by the wash-in of a contrast agent.

Thus, in at least one embodiment, the method determines a multiplicity of angiograms from rotating observation angles. However, no parallel projections are used in the process, because the longer scanning time of at least one half rotation would be required for this purpose. According to at least one embodiment of the invention, fan-shaped projections are used which originate from a single reading or from a few readings which are close to each other spatially and temporally. Knowledge of the location of the vessel to be observed and the geometric properties of the CT system allows the spatial reconstruction of the progress of the contrast agent bolus in the vessel from the multiplicity of projective angiograms from different positions of the radiation source, not in the sense of a CT reconstruction, but in the sense of a spatial calculation, and thus the velocity profile of a contrast agent front or a contrast agent bolus through a vessel can be displayed with a very high temporal resolution.

To allow the diagnostician to evaluate the measured data without problems, it is possible to subsequently output a three-dimensional view or else a slice image view, or possibly a smoothed view of the vessel, with it being possible for the velocity profile along the vessel to be represented by a graph or else by color-coding the velocity and superposing it on the voxels of the vessel.

In accordance with the basic idea of at least one embodiment of the invention described above, the inventors propose a method for measuring the flow rate of a contrast agent in at least one vessel of a patient by means of a computed tomography examination, the method comprising:

scanning the patient by x-rays emitted in a fan-shape on two planes and determining the absorption from a multiplicity of rotational angles while the contrast agent propagates through the at least one vessel, reconstructing at least one three-dimensional data record of local absorption data with the at least one vessel which can be filled by a contrast agent, determining in each case one set of x-rays which pass through this vessel for a multiplicity of temporally subsequent rotational angles of the x-rays emitted in a fan-shape, subsequently referred to as vessel/ray-sets, determining the changing absorption values along this vessel from the temporally subsequent vessel/ray-sets, and determining the propagation velocity of the contrast agent in this vessel from the spatial and temporal change of the absorption values in this vessel.

In an improvement of the method according to at least one embodiment of the invention, provision is made for the absorption through the patient without a contrast agent to be taken into account for every ray by using previously obtained absorption data when determining the absorption values of the vessel/ray-sets.

For this process, it is possible that the absorption data of the patient without a contrast agent is taken from previously determined tomographic data, or it is possible that the absorption data of the patient without a contrast agent is used directly from the projection data of a scan without a contrast agent.

Preferably, it is possible for the rays of the vessel/ray-sets to be combined such that the distances between their intersections and the vessel are equal. This makes it slightly easier to display the velocity properties of the contrast agent in the vessel.

It is also advantageous if the propagation velocity of the contrast agent in the vessel is calculated for each section of the section and illustrated in the form of a graph. In this case, it is possible to use a tracking chart to display the graph and to preferably show this three-dimensionally with a tomographic display of the vessel. Alternatively, it is also possible to use color-coding in the display of the graph and to superpose this on the vessel in a tomographic display of the vessel.

The method according to at least one embodiment of the invention can also be used by a CT system with a closed, rotating gantry, but it is particularly advantageous to apply the method in connection with a C-arm system because in that case the moveable C-arm is moved at a lower rate than is the case in a CT system with a rotating gantry, so that, in the case of flow rate measurements, a very high temporal resolution can also be achieved by a C-arm system.

Reference is made to the fact that a computational unit for evaluating the scanning information of a CT system or a C-arm machine with a program memory is within the scope of at least one embodiment of the invention, wherein the computational unit is intended to have program code in the program memory which implements the method according to at least one embodiment of the invention during operation.

BRIEF DESCRIPTION OF THE DRAWINGS

In the following text, the invention is described in more detail on the basis of an example embodiment with the aid of the figures, in which only the features required to understand the invention are illustrated. In this case, the following reference symbols are used: 1.1: x-ray CT system with a closed gantry; 1.2: C-arm system; 2: first x-ray tube; 3: first detector; 4: second x-ray tube; 5: second detector; 6: gantry housing/housing for the drive unit of the C-arm; 7: patient; 8: patient couch; 9: system axis; 10: computational unit; $11_{T1}$, $11_{T2}$: HU-value profile at time T1, T2; 12: front; 13: threshold; 14: stenoses; 15: velocity profile; $\alpha_i$: rotational angle; F: focus; G: vessel; $G_P$: projection of the vessel on the detector; $HU_G$: absorption values in the vessel in HU; $S_{G\alpha,i}$: vessel/ray-set; $Prg_1$-$Prg_n$: computer programs; S: bundle of rays; $S_G$: section of the vessel; T1, T2: time; $v_G$: propagation velocity of the contrast agent.

In detail.

DETAILED DESCRIPTION OF THE EXAMPLE EMBODIMENTS

Figure 1:
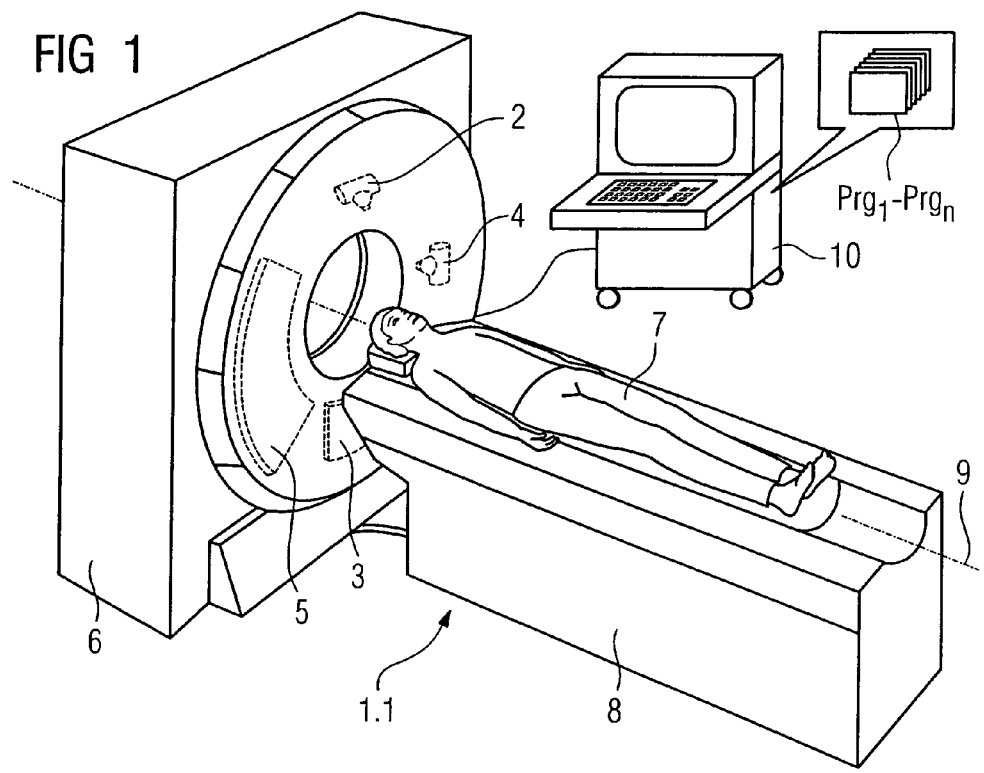
FIG. 1 shows an x-ray CT system.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 2:
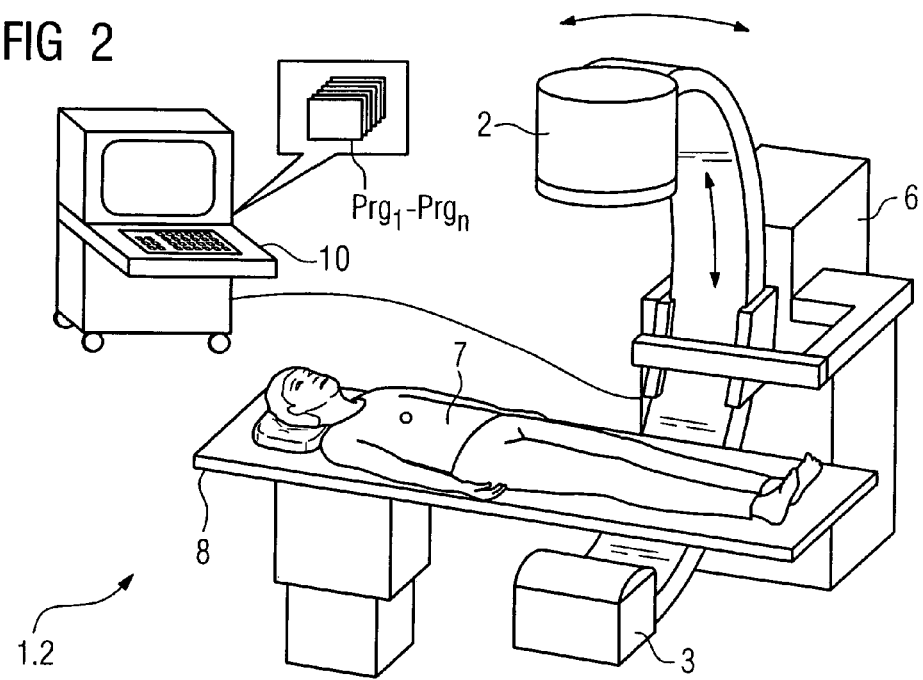
FIG. 2 shows a C-arm system.

FIGS. 1 and 2 show two possible machine variants by which the method according to an embodiment of the invention can be implemented.

FIG. 1 shows a conventional x-ray CT system 1.1 with a gantry housing, in which a first x-ray tube 2, with a first flat detector 3 opposite it, is arranged on the gantry (not illustrated here). Optionally, one or more further x-ray detector systems 4, 5 can also be arranged on this gantry and it is possible for them to be operated with different x-ray energy spectra. The patient 7 is located on a moveable patient couch 8, which for the purposes of scanning is drawn into the measuring field of the x-ray detector systems along a system axis 9. According to the invention, the patient is preferably scanned without being advanced along the z-axis, but detector systems are arranged at a sufficient radial distance from the system axis 9 that a relatively large region of the patient can be scanned during one rotation. The CT system itself is controlled by a computational unit 10 which can also simultaneously be operated as an evaluation unit. For this purpose, computer programs $Prg_1$-$Prg_n$ which can carry-out the method according to the invention are stored in the memory of the computational unit 10.

As an alternative to the x-ray CT system described above, a C-arm system 1.2, as shown in FIG. 2, can be used in the method according to an embodiment of the invention. Due to the relatively slow movement of the C-arm of this system in particular, the method according to an embodiment of the invention has major advantages for such a machine because the temporal resolution is particularly enhanced by the method according to the invention. The C-arm system 1.2 illustrated comprises an x-ray tube 2 with a flat detector 3 opposite it. Both are attached to a C-arm, which can be rotated in the housing 6 about a patient 7 on a patient couch 8 by way of the drive unit. A computational unit 10 is also available here, which can be used as an evaluation unit by executing computer programs $Prg_1$ to $Prg_n$ in the memory of this computational unit 10, which implement the method according to an embodiment of the invention.

Figure 3:
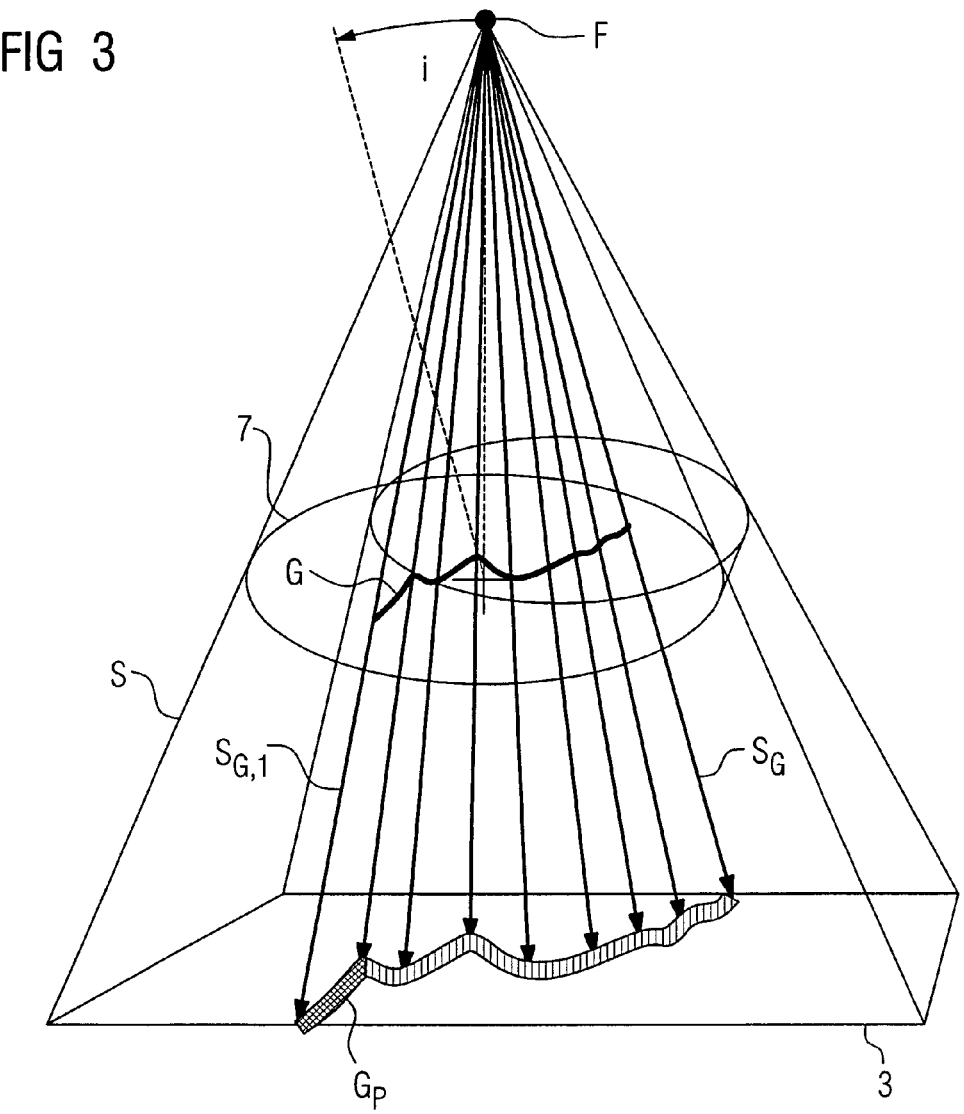
FIG. 3 shows a schematic illustration of a fan-shaped bundle of rays with a vessel/ray-set.

To aid understanding of the method according to an embodiment of the invention, a snapshot of a scan of a patient 7 by a bundle of rays S of a CT system is illustrated in FIG. 3. There is a vessel G in the patient 7, which can be localized with the aid of a previously conducted CT scan. It is particularly expedient in this case if the CT scan for localizing this vessel is conducted using a vessel filled with a contrast agent. However, it is also possible to localize the vessel without previously administering a contrast agent, by using a "dual energy" CT system, for example.

If the spatial profile of such a vessel in a patient is known, it is possible to find for each tube/detector position a set of x-rays, subsequently called vessel/ray-set $S_{G\alpha,i}$, which pass through the observed vessel G. On the detector 3 side, this vessel/ray-set images the projected profile of the vessel $G_P$ in the patient 7.

Knowledge of the absorption values of the patient without contrast agent allows removal by calculation of the absorption caused by the patient himself for the previously determined rays of the vessel/ray-set, so that only the absorption values which result from the influx of contrast agent in the vessel are generated. In the example shown here in FIG. 3, the contrast agent flows into the vessel from the left-hand side and has reached the points where the first two rays pass through from the left, while the rest of the vessel is not yet filled with a contrast agent.

Figure 4:
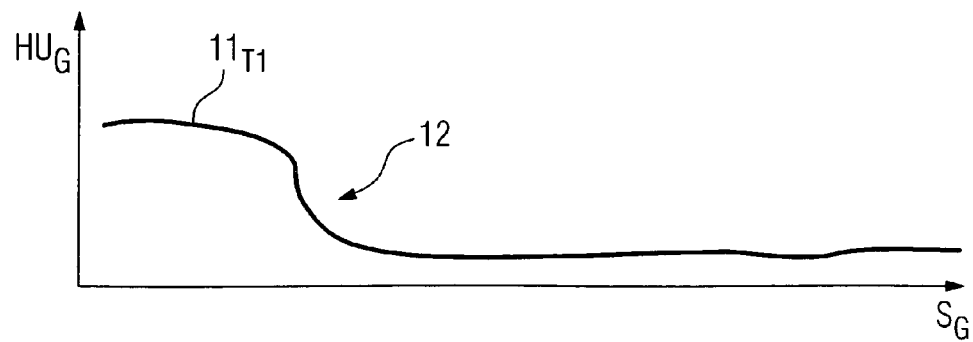
FIG. 4 shows the HU-value profile in the vessel of FIG. 3.

If these absorption values, for example in the form of HU values, are plotted on a graph against the section $S_G$ of the vessel, the current HU-value profile $11_{T1}$ at time T1 is obtained, as shown in FIG. 4, which corresponds to the snapshot in FIG. 3. It can be seen from this profile that the contrast agent forms a front 12, on which the HU-value increases rapidly. By way of example, the position of this front 12 can be measured with the aid of thresholding.

Figure 5:
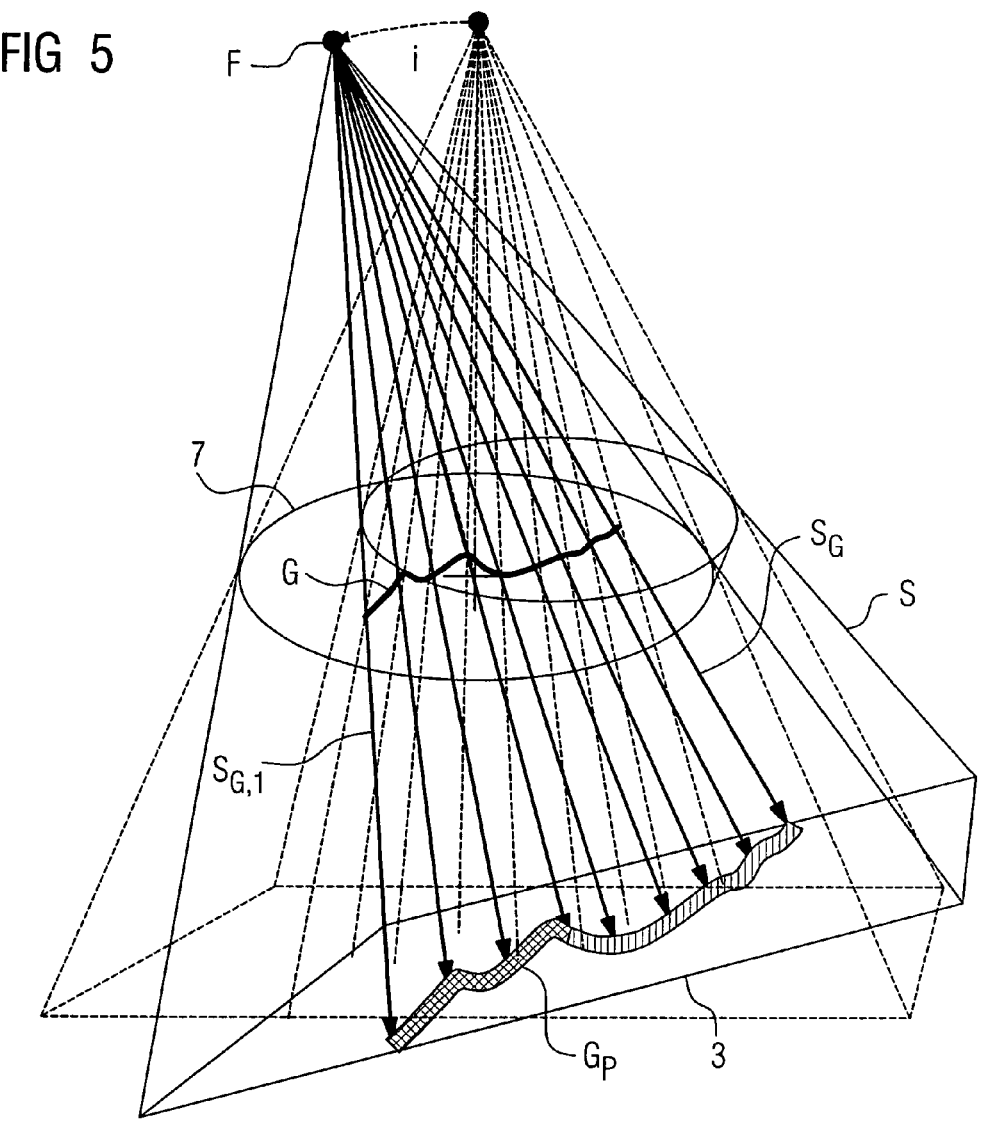
FIG. 5 shows the fan-shaped beam of the CT system from FIG. 3, rotated through the rotational angle $\alpha_i$.

FIG. 5 now shows a scanning situation at a later time, with the tube-detector system in, the meantime having been rotated through an angle $\alpha_i$. The rays in the position according to the snapshot of FIG. 3 are illustrated by dashed lines, while the solid lines show the bundle of rays S at the time of rotation through the angle $\alpha_i$. From the now changed angle $\alpha_i$, those rays which cut the vessel G from the changed observation angle also have to be found in this snapshot using the knowledge of the position of the vessel G. Of course, these are not the same rays as in FIG. 3. In this case it is also possible to calculate the absorption of the rays minus the absorption by the patient and to plot it on a graph. As can be seen in FIG. 5, the vessel G is now filled with contrast agent over a slightly longer section, so that, counting from the left, the first four rays of the vessel/ray-set see the contrast agent, while the remaining rays still pass through the vessel without a contrast agent.

Figure 6:
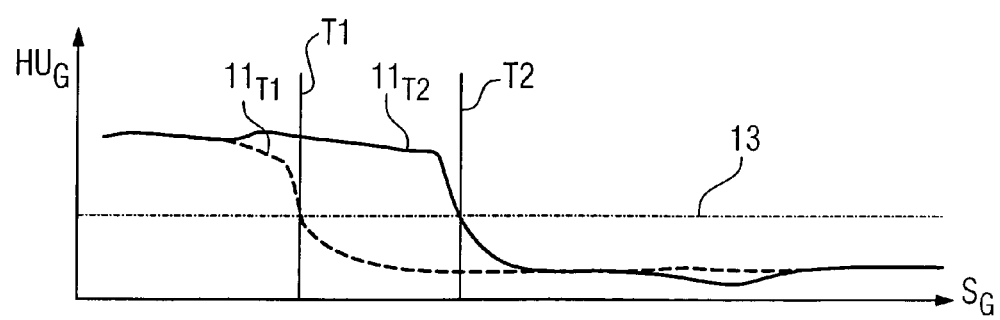
FIG. 6 shows an illustration of the advance of the contrast agent front in the vessel from FIG. 5.

If the absorption values are now plotted in turn against the section of the vessel $S_G$ on an HU tracking chart, this results in an absorption profile as is illustrated, for example, in FIG. 6 by the reference symbol $11_{T2}$. In addition, the absorption profile $11_{T1}$ at time T1 is illustrated by a dashed line and describes the advancing contrast agent front. For example, if a threshold 13 is set as the definition for the front of the contrast agent, the instantaneous velocity $V_G$ of the contrast agent, that is to say the flow rate, can be determined on the basis of the time that has passed between times T1 and T2 and the distance that the contrast agent has covered in the vessel.

The possible temporal resolution of this method is now no longer determined by the duration of a half rotation of the CT system, but by the interval between two readings, or the spatial resolution of the detector system.

Figure 7:
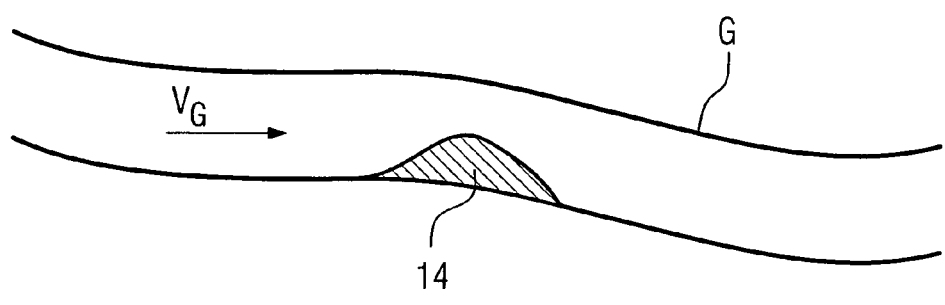
FIG. 7 shows a tomographic illustration of the observed vessel with the associated velocity profile of the contrast agent in the vessel illustrated below.
Figure 7:
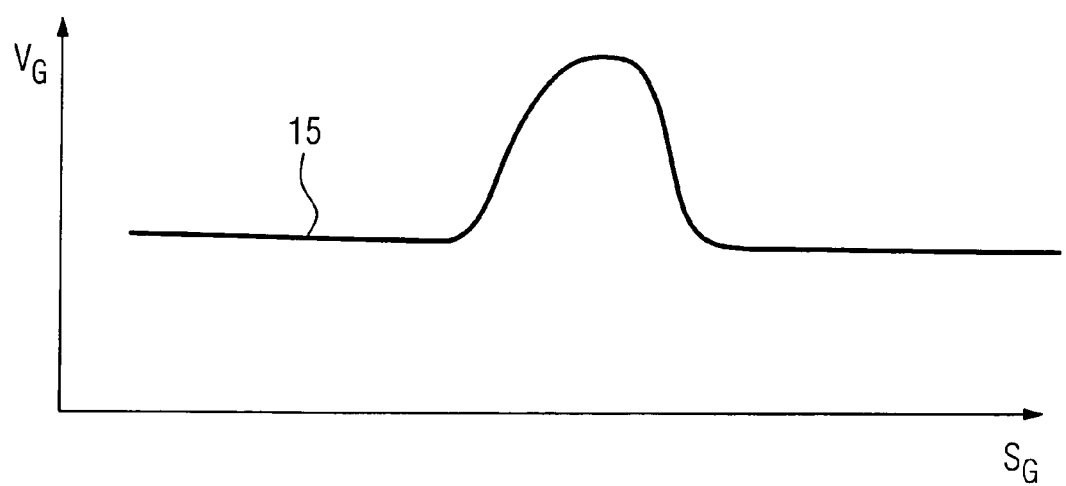

By way of example, it is now possible—as illustrated in FIG. 7—to show a vessel G in a slice image or in a three-dimensional tomographic illustration for a simplified diagnosis, with it being possible to show a velocity graph associates three-dimensionally with this vessel G, as shown at the bottom of FIG. 7. This velocity diagram shows the flow rate $v_G$ along the path $S_G$, with a significant temporary increase in the flow rate being observed in regions with stenoses 14. This is illustrated in an example manner by the velocity profile 15.

Overall, this results in a new, optimum diagnostic aid for detecting vessel stenoses or other illnesses affecting the perfusion by means of such a high resolution display of the flow rate in a vessel.

It is understood that the abovementioned features of the invention can be applied not only in the respectively stated combination, but also in other combinations or on their own, without departing from the scope of the invention.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for measuring a flow rate of a contrast agent in at least one vessel of a patient using a computed tomography examination, the method comprising:
    scanning the patient by x-rays, emitted in a fan-shape on two planes and determining absorption from a multiplicity of rotational angles while the contrast agent propagates through the at least one vessel of the patient;
    reconstructing at least one three-dimensional data record of local absorption data with the at least one vessel finable with a contrast agent;
    determining, for each of the two planes, one set of x-rays which pass through the at least one vessel for a multiplicity of temporally subsequent rotational angles of the x-rays emitted in a fan-shape, subsequently referred to as vessel/ray-sets, wherein the set of x-rays from one of the two planes corresponds to a projection taken at a different time than the set of x-rays from the other of the two planes;
    determining changing absorption values along the at least one vessel from the temporally subsequent vessel/ray-sets; and
    determining a propagation velocity of the contrast agent in the at least one vessel from the spatial and temporal change of the absorption values in the at least one vessel.

2. The method as claimed in claim 1, wherein the absorption through the patient without a contrast agent is taken into account for every ray by using the previously obtained absorption data when determining the absorption values of the vessel/ray-sets.

3. The method as claimed in claim 2, wherein the absorption data of the patient without a contrast agent is taken from previously obtained tomographic data.

4. The method as claimed in claim 2, wherein the absorption data of the patient without a contrast agent is taken from the projection data of a scan without a contrast agent.

5. The method as claimed in claim 1, wherein the rays of the vessel/ray-sets are combined such that the distances between their intersections and the vessel are equal.

6. The method as claimed in claim 1, wherein the propagation velocity of the contrast agent in the vessel is calculated for each section of the section and illustrated in the form of a graph.

7. The method as claimed in claim 6, wherein a tracking chart is used to display the graph and is shown three-dimensionally with a tomographic display of the vessel.

8. The method as claimed in claim 6, wherein color-coding is used in the display of the graph and is superposed on the vessel in a tomographic display of the vessel.

9. The method as claimed in claim 1, wherein the reconstruction of the at least one three-dimensional data record of local absorption data for determining the position of the at least one vessel finable by a contrast agent takes place using scan data recorded of a vessel completely filled with a contrast agent.

10. The method as claimed in claim 1, wherein a CT system with a rotating gantry is used to scan the patient.

11. The method as claimed in claim 1, wherein a C-arm system with a moveable C-arm is used to scan the patient.

12. A system for evaluating scanning information, comprising:
    an x-ray system configured for scanning a patient by x-rays emitted in a fan-shape on two planes and determining absorption from a multiplicity of rotational angles while a contrast agent propagates through at least one vessel of the patient;
    a computational unit configured for reconstructing at least one three-dimensional data record of local absorption data with the at least one vessel fillable with a contrast agent;
    a detector system configured for, for each of the two planes, determining one set of x-rays which pass through the at least one vessel for a multiplicity of temporally subsequent rotational angles of the x-rays emitted in a fan-shape, subsequently referred to as vessel/ray-sets, wherein the set of x-rays from one of the two planes corresponds to a projection taken at a different time than the set of x-rays from the other of the two planes, wherein the computational unit is configured for determining changing absorption values along the at least one vessel from the temporally subsequent vessel/ray-sets; and an evaluation unit configured for determining a propagation velocity of the contrast agent in the at least one vessel from the spatial and temporal change of the absorption values in the at least one vessel.

13. The system of claim 12, wherein the system is a CT system and wherein the x-ray system includes a rotating gantry to scan the patient.

14. The system of claim 12, wherein the system is a CT system and wherein the x-ray system includes a moveable C-arm to scan the patient.

15. A system for evaluating scanning information, comprising:

at least one of a rotating gantry and a movable C-arm to scan the patient by x-rays emitted in a fan-shape on two planes, wherein absorption is determined from a multiplicity of rotational angles while a contrast agent propagates through at least one vessel of the patient;

a computational unit configured for reconstructing at least one three-dimensional data record of local absorption data with the at least one vessel finable with a contrast agent;

a detector system configured for determining, for each of the two planes, one set of x-rays which pass through the at least one vessel for a multiplicity of temporally subsequent rotational angles of the x-rays emitted in a fan-shape, subsequently referred to as vessel/ray-sets, wherein the set of x-rays from one of the two planes corresponds to a projection taken at a different time than the set of x-rays from the other of the two planes, wherein the computational unit is configured for determining changing absorption values along the at least one vessel from the temporally subsequent vessel/ray-sets; and an evaluation unit configured for determining a propagation velocity of the contrast agent in the at least one vessel from the spatial and temporal change of the absorption values in the at least one vessel.

16. A computational unit for evaluating scanning information of at least one of a CT system and C-arm machine, comprising:

a non-transitory computer readable medium storing a program which, during operation, causes the computational unit to measure a flow rate of a contrast agent in at least one vessel of a patient using a computed tomography examination by, scanning the patient by x-rays, emitted in a fan-shape on two planes and determining absorption from a multiplicity of rotational angles while the contrast agent propagates through the at least one vessel of the patient;

reconstructing at least one three-dimensional data record of local absorption data with the at least one vessel fillable with a contrast agent;

determining, for each of the two planes, one set of x-rays which pass through the at least one vessel for a multiplicity of temporally subsequent rotational angles of the x-rays emitted in a fan-shape, subsequently referred to as vessel/ray-sets, wherein the set of x-rays from one of the two planes corresponds to a projection taken at a different time than the set of x-rays from the other of the two planes;

determining changing absorption values along the at least one vessel from the temporally subsequent vessel/ray-sets; and determining a propagation velocity of the contrast agent in the at least one vessel from the spatial and temporal change of the absorption values in the at least one vessel.

* * * * *